Figure 1:
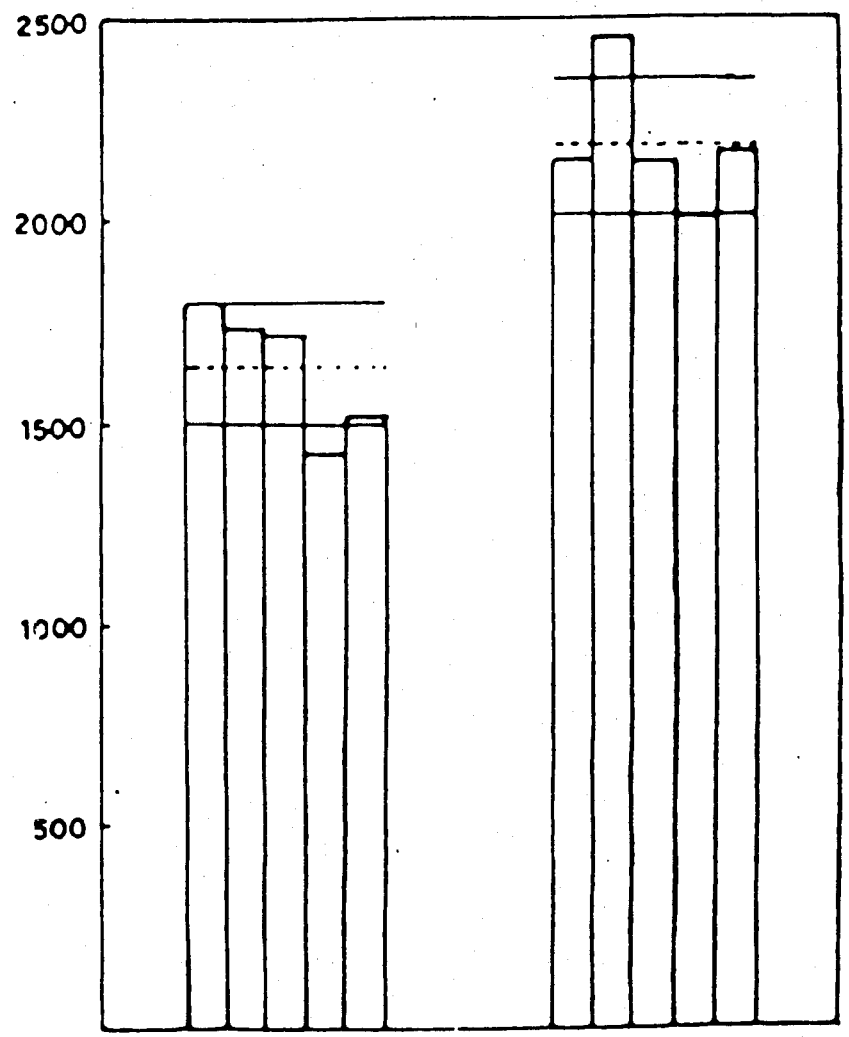

United States Patent [19]

Scolastico et al.

[11] Patent Number: 4,624,946

[45] Date of Patent: Nov. 25, 1986

[54] TREATMENT OF INVOLUTIONAL BRAIN SYNDROMES AND MENTAL DECAY

[75] Inventors: Carlo Scolastico, Milan; Gabriele Braglia, Carimate, both of Italy

[73] Assignee: LPB Istituto Farmaceutico S.p.A., Cinisello Balsamo, Italy

[21] Appl. No.: 760,955

[22] Filed: Jul. 31, 1985

[30] Foreign Application Priority Data

May 8, 1985 [IT]  Italy ............................... 48055 A/85

[51] Int. Cl.$^4$ ........................................... A61K 31/685
[52] U.S. Cl. ..................................................... 514/77
[58] Field of Search ......................................... 514/77

[56] References Cited

FOREIGN PATENT DOCUMENTS

25706A/79  9/1979  Italy .

*Primary Examiner*—Stanley J. Friedman
*Attorney, Agent, or Firm*—Bucknam and Archer

[57] ABSTRACT

Pharmaceutical compositions, containing L-alpha-glycerylphosphorylcholine, are effective for the treatment of brain involutional syndromes of an essential, vascular or traumatic origin, and of the mental decay in the elderly.

1 Claim, 2 Drawing Figures

TREATMENT OF INVOLUTIONAL BRAIN SYNDROMES AND MENTAL DECAY

The invention concerns pharmaceutical compositions containing, as active ingredient, L-alpha-glycerylphosphorylcholine (possibly combined with other drugs active on the central nervous system), suited for the treatment of brain involutional syndromes of an essential, vascular or traumtic origin, and of the mental decay in the eldery.

L-ALPHA-GLYCERYLPHOSPHORYLCHOLINE (I)

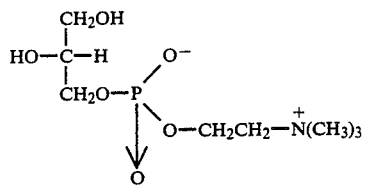

is known to exert a therapeutic activity in patients affected with anomalies in lipid metabolism, acute, subacute and chronic hepatitis, steatosis, and analogous pathologic forms: see in this connection the Italian Patent Application by the Applicant, No. 25706 A/79, filed on 9-14-1979.

L-Alpha-glycerylphosphorylcholine, when given orally or parenterally, has now surprisingly been found to exert a quite interesting activity also on the central nervous system, in terms of an activation of the central cholinergic system, and indirectly of the functionally related dopaminergic system. The pharmacological results are hereinbelow reported.

1. EFFECTS ON THE DOPAMINE TURNOVER

Male rats, given oral or intraperitoneal increasing doses of L-alpha-glycerylphosphorylcholine were sacrificed 2 hours after the treatment. The striatal concentrations of 3,4-dihydroxyphenylacetic acid (DOPAC) were measured by HPLC, using an inverse phase column according to the method of L. J. Felice et al., *J. Neurochem.*, 31, 1461–1467, 1978. Table 1 shows that the compound induces a significant increase of the striatal concentrations of DOPAC at doses higher than 80 $\mu$Moles/kg. Said increase persists for at least 4 hours (Table 2).

TABLE 1

EFFECT OF THE INTRAPERITONEAL OR ORAL ADMINISTRATION OF VARIOUS DOSES OF L-ALPHA-GLYCEROLPHOSPHORYLCHOLINE ON THE STRIATAL CONCENTRATIONS OF 3,4-DIHYDROXYPHENYLACETIC ACID

| Dose ($\mu$Moles/kg) 2 hours before the sacrifice | Administration route | |
|---|---|---|
| | Intraperitoneal | Oral |
| | DOPAC ng/mg tissue | |
| — | 2.45 ± 0.27 | 2.40 ± 0.30 |
| 10 | 2.49 ± 0.17 | 2.37 ± 0.21 |
| 20 | 2.30 ± 0.34 | 2.19 ± 0.27 |
| 80 | 2.87 ± 0.34** | 2.76 ± 0.24* |
| 160 | 3.55 ± 0.25** | 3.50 ± 0.19** |
| 240 | 3.69 ± 0.25** | 3.65 ± 0.24** |

The values represent the means ± SD of 8 animals in each group of treatment.
*P <0.05;
**P <0.01 Dunnet's t-test.

TABLE 2

STRIATAL CONCENTRATIONS OF 3,4-DIHYDROXYPHENYLACETIC ACID AT VARIOUS TIME AFTER THE INTRAPERITONEAL AND ORAL ADMINISTRATIONS OF L-ALPHA-GLYCERYL-PHOSPHORYLCHOLINE (160 $\mu$Moles/kg)

| Time | Administration route | |
|---|---|---|
| | Intraperitoneal | Oral |
| Control | 2.39 ± 0.22 | 2.50 ± 0.30 |
| 1 h | 3.75 ± 0.27** | 3.20 ± 0.18** |
| 2 h | 3.96 ± 0.18** | 3.84 ± 0.17** |
| 4 h | 2.88 ± 0.25** | 3.30 ± 0.21** |

The values are the means ± SD of 8 animals in each group of treatment, and are expressed as ng/mg of tissue
**P < 0.01 Dunnet's t-test.

2. EFFECT ON THE DOPAMINE RELEASE

The dopamine release was assessed on slices of rat striatum (300×300$\mu$) taken out 2 hours after the oral treatment with L-alpha-glycerylphosphorylcholine (alpha-GPC) (240 $\mu$Moles/kg). The slices were preincubated with oxygenated Krebs-Ringer's fluid containing $^3$H-dopamine (0.4 $\mu$Ci/ml, $10^{-7}$M) and $CaCl_2$ that favors the tissue uptake. Subsequently, the incubation medium was added with KCl (50 $\mu$Moles) as depolarizing agent, and the radioactivity liberated in the medium, during 10 minutes, was assessed by a liquid phase scintillation spectrometer. FIG. 1 shows that the in vivo treatment with the compound produces an increase of the capacities of the striatum slices, prepared from the treated animals, to liberate in vitro dopamine following a depolarizant stimulus.

In FIG. 1 the horizontal broken and solid lines indicate the means and the standard deviations, respectively, of the experimental groups. The basal release proved equivalent to 3022±546 and 2904±453 dpm/mg protein/10 min for the control and the treated animals respectively.

3. INVESTIGATIONS ON THE BINDING WITH THE CHOLINERGIC RECEPTORS

Figure 2:
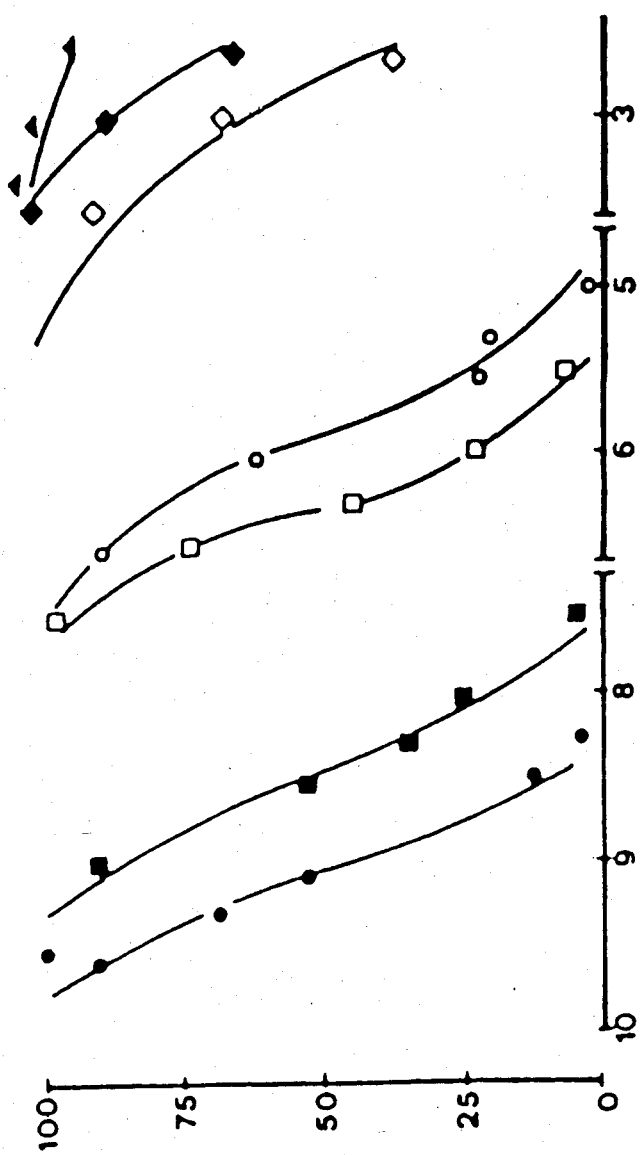

The investigation on the cholinergic receptors on in toto rat's brain was carried out using the method of H. Yamamura and S. H. Suyder, *Mol. Pharmacol.*, 10, 861–867, 1974, using $^3$H-quinonuclyldibenzylate (QNB) as the binding agent. L-Alpha-glycerylphosphorylcholine and the reference compounds were incubated at concentrations ranging between $5 \times 10^{-10}$ and $5 \times 10^{-3}$ moles for 60' at 25° C. FIG. 2, in which the various symbols, have the below reported significances, i.e.:

| ( ) QNB | ( ) Choline |
|---|---|
| ( ) Atropine | ( ) Alpha-glycerolphosphorylcholine |
| ( ) Oxotremorine | |
| ( ) Acetylcholine | ( ) Lecithin | states that L-alpha-glycerylphosphorylcholine cannot significantly bind in vitro with the cholinergic receptor. This evidence suggests that the in vitro activity on the cholinergic transmission is indirect, mediated possibly by an increased synthesis of acetylcholine.

4. DISTRIBUTION OF $^3$H(Me)-L-ALPHA-GLYCERYLPHOSPHORYL-CHOLINE IN THE BRAIN TISSUES

Some rats were given orally and intraperitoneally the labelled compound (20–100 μCi/kg), varying the doses following dilution with the cold drug), specific activity 45 μCi/mg. The experimental animals were sacrificed at various times after the treatment, and the brains dissected in the various areas; blood was also taken out in parallel. The radioactivity, present in the tissues, was counted in a liquid phase scintillation spectrometer.

The data reported in Table 3 state that L-alpha-glycerylphosphorylcholine (80 μMoles/kg), given orally and intraperitoneally, attains significant concentrations in various areas of the central nervous system.

As shown in Table 4, after oral administration a good relationship is found between the administered dose and the quantity of L-alpha-glycerylphosphorylcholine that attains the various brain areas.

TABLE 3

ACTIVITY (dpm/g) AT VARIOUS TIMES, AND IN VARIOUS BRAIN AREAS, AFTER INTRAPERITONEAL AND ORAL ADMINISTRATION OF 3H—ALPHA-GLYCERYLPHOSPHORYLCHOLINE (80 μMoles/kg, 100 μCi/kg)

| Administration route | Time h | Activity (dpm/g × $10^{-2}$) | | | | |
|---|---|---|---|---|---|---|
| | | Cortex | Cerebellum | Striatum | Hippocampus | Hypothalamus |
| Intraperitoneal | 0.5 | 485 ± 188 | 485 ± 188 | 426 ± 102 | 411 ± 123 | 573 ± 188 |
| | 1 | 676 ± 41 | 629 ± 68 | 512 ± 85 | 435 ± 96 | 1206 ± 532 |
| | 2 | 803 ± 101 | 779 ± 15 | 638 ± 75 | 568 ± 141 | 1155 ± 406 |
| | 4 | 688 ± 287 | 612 ± 329 | 571 ± 229 | 450 ± 223 | 1152 ± 44 |
| | 8 | 291 ± 156 | 232 ± 29 | 259 ± 6 | 132 ± 23 | 570 ± 100 |
| Oral | 1 | 790 ± 182 | 659 ± 146 | 646 ± 123 | 717 ± 197 | 1797 ± 326 |
| | 2 | 1064 ± 179 | 768 ± 126 | 197 ± 203 | 936 ± 69 | 1524 ± 19 |
| | 4 | 564 ± 119 | 488 ± 129 | 491 ± 87 | 420 ± 75 | 1136 ± 53 |
| | 8 | 706 ± 64 | 685 ± 31 | 644 ± 100 | 647 ± 123 | 953 ± 76 |

The values are the means ± SD of 8 animals in each experimental group.

TABLE 4

ESTIMATED CONCENTRATIONS OF L-ALPHA-GLYCERYLPHOSPHORYLCHO-LIONE IN VARIOUS BRAIN AREAS, 1 HOUR AFTER THE ADMINISTRATION OF VARIOUS DOSES OF THE DRUG

| | L-alpha-glycerylphosphorylcholine (nmoles/g tissue[1]) | | | |
|---|---|---|---|---|
| | Dose | | | |
| Area | 5 μMoles/kg | 10 μMoles/kg | 20 μMoles/kg | 80 μMoles/kg |
| Hypothalamus | 9.1 ± 2.33 | 13.56 ± 1.24 | 20.4 ± 6.18 | 65.3 ± 11.8 |
| Cerebellum | 2.0 ± 0.20 | 3.4 ± 0.86 | 4.1 ± 0.40 | 24.0 ± 5.34 |
| Hippocampus | 3.0 ± 0.26 | 4.9 ± 1.13 | 6.1 ± 1.87 | 26.0 ± 7.16 |
| Striatum | 4.7 ± 2.27 | 7.28 ± 2.14 | 10.7 ± 2.41 | 23.5 ± 4.47 |
| Cortex | 6.9 ± 0.97 | 10.2 ± 2.07 | 12.7 ± 4.14 | 29.1 ± 6.61 |

The values are the means ± SD of 8 animals in each experimental group.
[1]Calculated from (dpm/g tissue):(dpm/mole).

The hereinabove reported results induced to extend clinically the investigation, with specific reference to the symptomatic pattern associated with an insufficient cholinergic function, i.e. loss of memory, manias, behavioral disturbances, and so on. L-Alpha-glycerylphosphorylcholine was consequently confirmed to be a real and effective therapeutic agent, as confirmed by the below reported observations.

CLINICAL TRIALS

1. INVESTIGATION ON THE BRAIN SYNDROMES OF AN ESSENTIAL VASCULAR OR TRAUMATIC ORIGIN

Markedly positive results were obtained in initial involutional syndromes on which L-alpha-glycerylphosphorylcholine could exert a positive action on the basic neurophysiological mechanisms. Forty patients, affected by a brain syndrome of a vascular nature or of an Alzheimer-type, showed a significant improvement of the neurologic pattern (short- and medium-term memory, cognitive functions) that could also be evidenced by the EEG tracings, altered before the treatment.

L-Alpha-glycerylphosphorylcholine, given to 20 patients with head trauma, produced a significant regression of all neuropsychic symptoms of the post-concussional syndrome (headache, dizziness, balance disturbances): this regression was matched by a normalization of the acoustic evoked potentials of the brainstem (Baer).

2. INVESTIGATION ON THE MENTAL DECAY IN THE ELDERLY

The treatment with L-alpha-glycerylphosphorylcholine induced, in ζelderly patients with mental decay, a clear improvement of the mental tests, pertaining to attention, recent memory and cognitive abilities. Said results are to be referred to the participation of the drug in the activation of the memory function, and particularly of the cortex interneuronal connections impaired in the process of senile decay.

L-Alpha-glycerylphosphorylcholine, assessed in two controlled clinical trials, versus cytidindiphosphocholine, in 70 patients with an essential or vascular senile decay, proved to be able to improve the psychointellective conditions of the patient, and to attenuate the initially existent neurological symptomatic pattern; the positive recovery of recent memory, time-space disorientation and confusional state shall be specifically underlined. Said results are superimposable to the ones observed with the reference drug.

Moreover, the present invention concerns all industrially applicable aspects associated with the use of L-alpha-glycerylphosphorylcholine as a therapeutic agent to be used in the treatment of involutional brain syndromes of an essential vascular or traumatic origin and in the treatment of the mental decay in the elderly. Therefore, an essential aspect of the investigation covers pharmaceutical compositions containing, as active ingredient, prescheduled and therapeutically effective quantities of L-alpha-glycerylphosphorylcholine, possibly in mixture with excipients of current use in drug compounding, and possibly in mixture with other active ingredients, said compositions being however scheduled for the treatment of the above stated pathologic forms.

Unlimiting examples of pharmaceutical compositions, according to the present invention, are represented by:
(a) soft-gelatin capsules, containing 400 mg of L-alpha-glycerylphosphorylcholine, to be taken 2-3 times daily according to medical prescription;
(b) ampuls of 1000 mg of L-alpha-glycerylphosphorylcholine, for intramuscular injection, their contents to be injected once daily; (c) ampuls of 400 mg of L-alpha-glycerylphosphorylcholine for IV drip infusion, their contents to be injected at the rate of 1-6 daily, according to medical prescription.

We claim:
1. The method of treatment of a living subject affected by brain involutional syndromes of an essential, vascular or traumatic origin, and of the mental decay in the elderly which consists of administering to said living subject in need of treatment an effective amount of L-alpha-glycerylphosphorylcholine orally or parenterally.

* * * * *